US00PP11963P2

(12) United States Plant Patent
van Veen

(10) Patent No.: US PP11,963 P2
(45) Date of Patent: Jun. 26, 2001

(54) ASTILBE PLANT NAMED 'PINK LIGHTNING'

(75) Inventor: Wim van Veen, Noorden (NL)

(73) Assignee: Future Plants V.O.F., Noordwijk (NL)

( * ) Notice: Subject to any disclaimer, the term of this patent is extended or adjusted under 35 U.S.C. 154(b) by 0 days.

(21) Appl. No.: 09/473,565

(22) Filed: Dec. 29, 1999

(51) Int. Cl.[7] ..... A01H 5/00

(52) U.S. Cl. ..... Plt./263

(58) Field of Search ..... Plt./263

*Primary Examiner*—Bruce R. Campell
*Assistant Examiner*—Kent L. Bell
(74) *Attorney, Agent, or Firm*—C. A. Whealy

(57) ABSTRACT

A distinct cultivar of Astilbe plant named 'Pink Lightning', characterized by its upright and compact growth habit; dark green glossy leaves; very freely and uniformly flowering; and attractive light pink-colored flowers.

2 Drawing Sheets

BACKGROUND OF THE INVENTION

The present invention relates to a new and distinct cultivar of Astilbe plant, botanically known as Astilbe hybrid, and hereinafter referred to by the cultivar name 'Pink Lightning'.

The new cultivar is a product of a planned breeding program conducted by the Inventor in Noorden, The Netherlands. The objective of the breeding program was to develop new Astilbe cultivars with glossy leaves and attractive flower color.

The new cultivar originated from a cross made by the Inventor in 1993 of the Astilbe×Arendsii cultivar 'Bressingham Beauty', not patented, as the male or pollen parent, with the *Astilbe simplicifolia* cultivar 'Jaqueline', not patented, as the female or seed parent.

The cultivar 'Pink Lightning' was discovered and selected by the Inventor as a flowering plant within the progeny of the stated cross in a controlled environment in Noorden, The Netherlands.

Asexual propagation of the new cultivar by divisions harvested at Noorden, The Netherlands, has shown that the unique features of this new Astilbe are stable and reproduced true to type in successive generations.

SUMMARY OF THE INVENTION

Plants of the cultivar 'Pink Lightning' have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Pink Lightning'. These characteristics in combination distinguish 'Pink Lightning' as a new and distinct cultivar:

1. Upright and compact growth habit.
2. Dark green glossy leaves.
3. Very freely and uniformly flowering.
4. Attractive light pink-colored flowers.

Plants of the new Astilbe differ from plants of the male parent, the cultivar 'Bressingham Beauty', in leaf shape and flower color, in addition, plants of the new Astilbe are more compact and have glossier leaves than plants of the cultivar 'Bressingham Beauty'.

Plants of the new Astilbe are more compact and have glossier leaves than plants of the female parent, the cultivar 'Jaqueline'.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new Astilbe.

The photograph on the first sheet comprises a side perspective view of a typical plant of the new Astilbe.

The photograph at the top of the second sheet comprises a close-up view of a typical inflorescence of the new Astilbe.

The photograph at the bottom of the second sheet comprises a close-up view of typical leaves of the new Astilbe.

DETAILED BOTANICAL DESCRIPTION

In the following description, color references are made to The Royal Horticultural Society Colour Chart except where general terms of ordinary dictionary significance are used. Plants used for the description were about one year-old and grown in 17-cm containers under outdoor production conditions which closely approximate commercial production conditions during the spring and summer in Noorden, The Netherlands.

Botanical classification: Astilbe hybrid cultivar 'Pink Lightning'.

Parentage:

*Female parent.*—*Astilbe simplicifolia* cultivar 'Jaqueline', not patented.

*Male parent.*—Astilbe×Arendsii cultivar 'Bressingham Beauty', not patented.

Propagation:

*Type.*—By root divisions.

*Time to rooting.*—About 3 months at temperatures about 18° C.

*Root description.*—Fine.

Plant description:

*Crop time.*—From divisions, about 40 weeks are required to produce fully-grown flowering plants in 17-cm containers.

*Form.*—Upright, compact; inverted triangle.

*Branching habit.*—Flowering stems and leaves arise from the roots.

*Plant height.*—About 50 cm.

*Area of spread.*—About 40 cm.

*Vigor.*—Moderate.

*Stems.*—Length: About 50 cm. Internode length: About 8 cm. Texture: Pubescent; brownish hairs of various lengths. Color: 138B to 139B to 139C.

*Foliage description.*—Arrangement: Bi-ternately compound; alternate. Quantity of leaflets per leaf: Typically about 25 to 30. Leaf length, including petiole: About 20 cm. Leaf width: About 12 cm. Leaflet shape: Ovate to elliptic. Leaflet apex: Acuminate. Leaflet base: Rounded to acuminate. Leaflet margin: Doubly serrate; slightly wavy. Leaflet texture: Glossy, lustrous; lower surface very sparsely covered with very short (less than 0.5 mm ) gray hairs; fewer hairs on upper surface. Leaflet color: Young and mature foliage, upper surface: 147A to 139A. Young and mature foliage, lower surface: 137B to 137C. Venation, upper surface: 137B to 137C. Venation, lower surface: 138A. Petiole: Length: About 8 cm. Diameter: About 3 mm. Texture: Very sparsely covered with very short (less than 0.5 mm) gray hairs. Color: 138B to 139B to 139C; 183A at base.

Flower description:

*Flower type and habit.*—Numerous small single flowers arranged in branched panicles. Very freely flowering with about 1,600 flowers and flower buds per plant. Flowers sessile.

*Natural flowering season.*—Continuously flowering typically during the early summer.

*Flower longevity.*—Flowers last a few weeks on the plant and more than one week as a cut flower. Flowers persistent.

*Fragrance.*—Sweet, pleasant.

*Flower buds.*—Length: About 3 mm. Diameter: About 2 mm. Shape: Ovate to orbicular. Rate of opening: About three weeks from visible bud to fully opened flower. Color: 62A.

*Flower size.*—Length (height): About 5 mm. Diameter: About 1.2 cm.

*Petals.*—Arrrangement: Five. Shape: Oblanceolate. Apex: Obtuse. Margin: Entire. Length: About 6 mm. Width: About 2 mm. Texture: Smooth. Color: When opening, upper and lower surfaces: 62B. Fully opened flower, upper and lower surfaces: 62C to 62D; fading to slightly paler than 62D.

*Calyx.*—Length: About 3 mm. Width: About 5 mm. Number of sepals: About five. Sepal shape: Ovate. Sepal apex: Obtuse. Sepal margin: Entire. Sepal color (Both surfaces): Close to 155A to 157D.

*Reproductive organs.*—Stamens: Stamen number: About ten. Anther attachment: Basifixed. Anther length: Less than 0.5 mm. Anther color: Creamy white. Pollen amount: Scarce. Pollen color: Creamy white. Pistils: Pistil number: Two. Pistil length: About 2.5 mm. Stigma shape: Club-shaped. Stigma color: 58C. Style length: About 2 mm. Style color: 58C. Ovary color: 150D.

*Seed.*—Length: Less than 0.5 mm. Diameter: Less than 0.5 mm. Color: Light brown.

Disease resistance: Under commercial conditions, plants of the new Astilbe have exhibited some resistance to diseases common to Astilbe.

It is claimed:

1. A new and distinct cultivar of Astilbe plant named 'Pink Lightning', as illustrated and described.

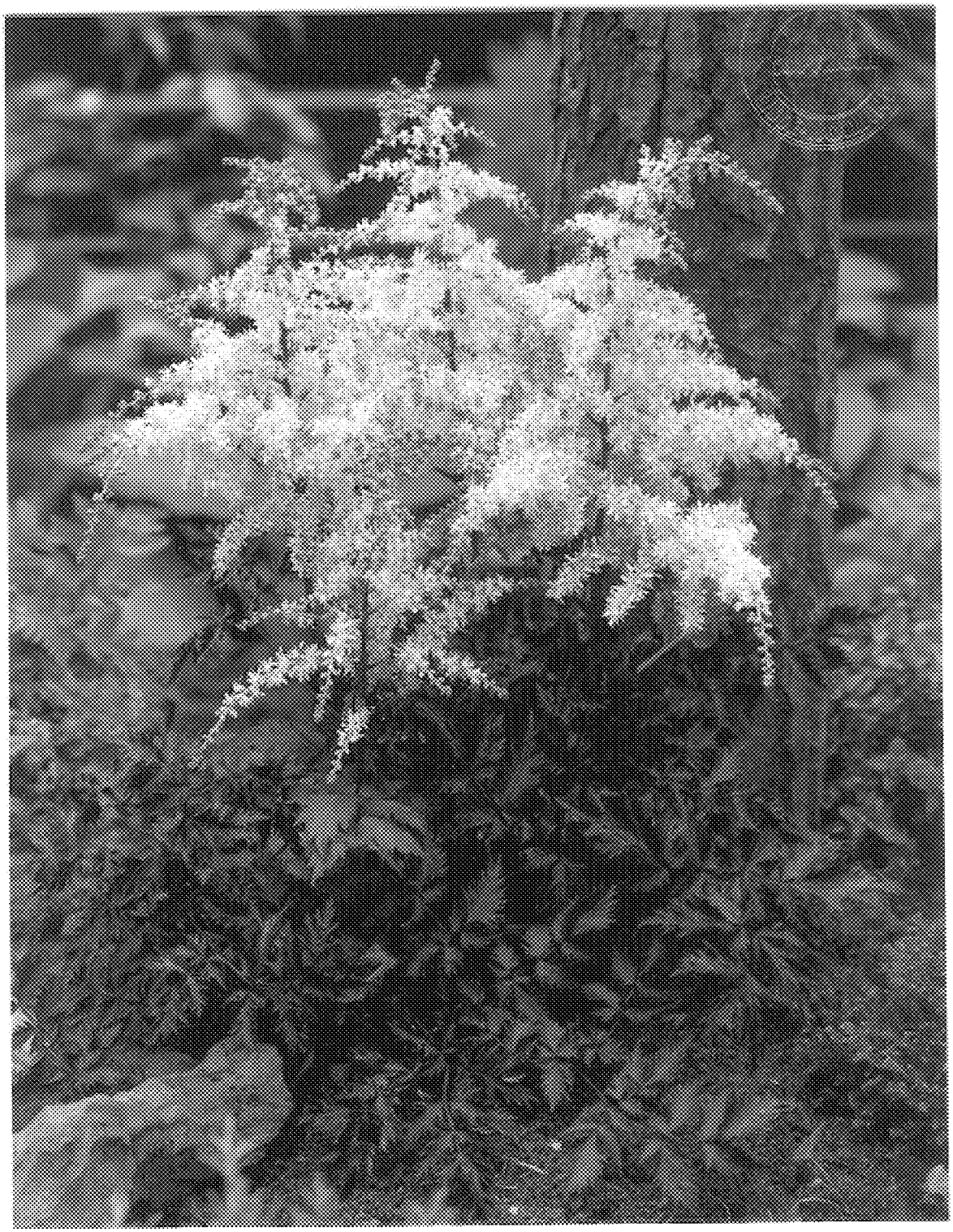

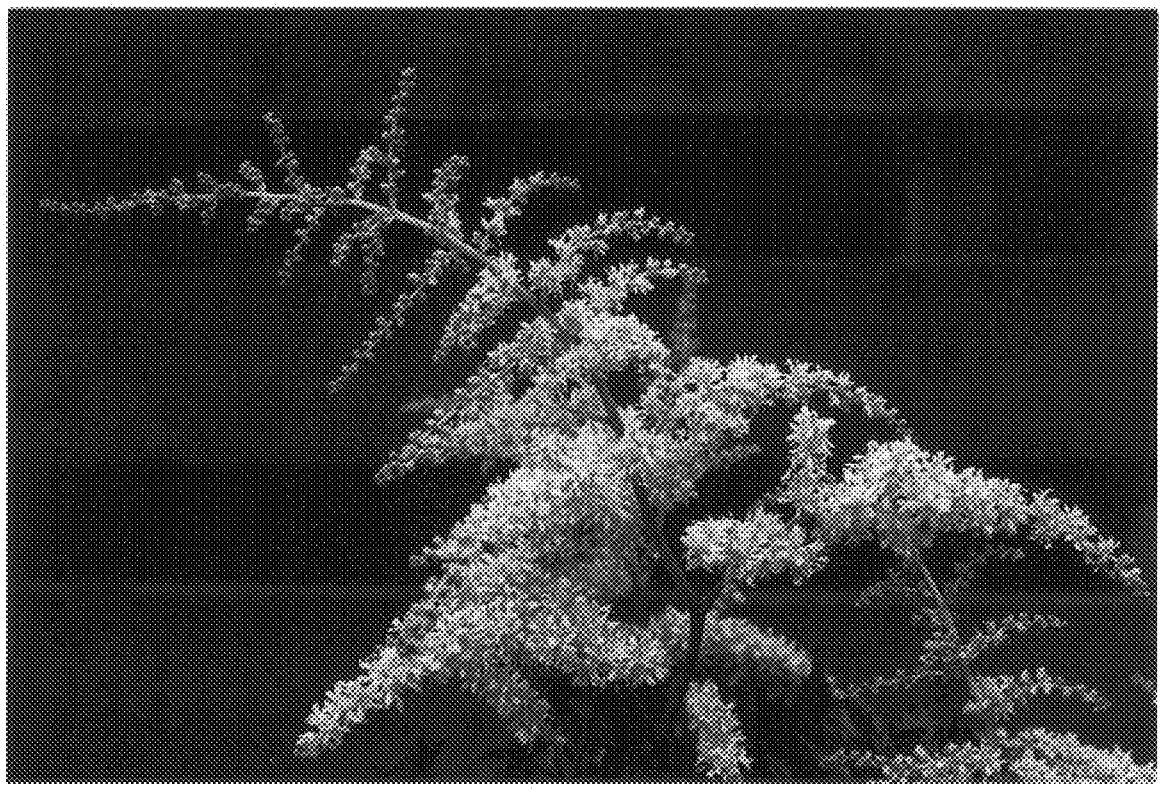
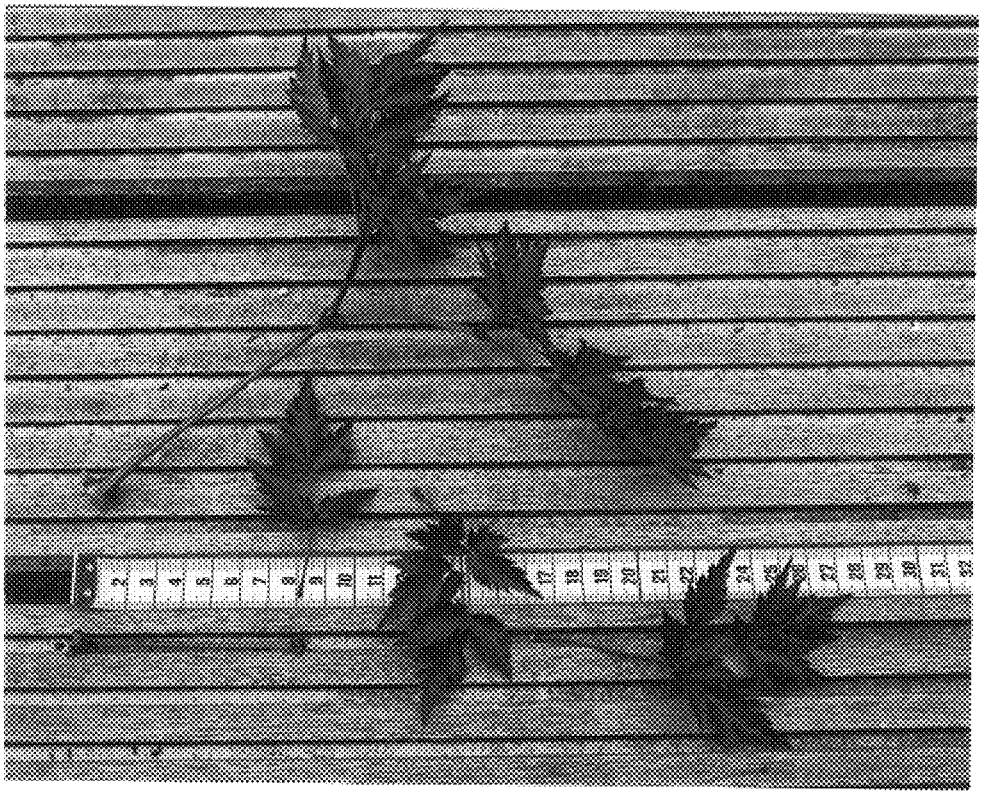

* * * * *